United States Patent
Pfeiffer et al.

(10) Patent No.: US 8,919,192 B2
(45) Date of Patent: Dec. 30, 2014

(54) MULTIVARIABLE SENSOR FOR DETERMINING AND/OR MONITORING FILL LEVEL AND DENSITY AND/OR VISCOSITY OF A LIQUID IN A CONTAINER

(75) Inventors: Helmut Pfeiffer, Steinen (DE); Alexander Muller, Sasbach-Jechtingen (DE); Volker Dryer, Lorrach (DE); Sergej Lopatin, Lorrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 161 days.

(21) Appl. No.: 13/390,160

(22) PCT Filed: Jul. 21, 2010

(86) PCT No.: PCT/EP2010/060521
§ 371 (c)(1),
(2), (4) Date: Feb. 13, 2012

(87) PCT Pub. No.: WO2011/018312
PCT Pub. Date: Feb. 17, 2011

(65) Prior Publication Data
US 2012/0144901 A1    Jun. 14, 2012

(30) Foreign Application Priority Data
Aug. 14, 2009    (DE) .......................... 10 2009 028 548

(51) Int. Cl.
| | | |
|---|---|---|
| *G01F 23/00* | (2006.01) | |
| *G01F 23/296* | (2006.01) | |
| *G01N 9/32* | (2006.01) | |
| *G01N 11/16* | (2006.01) | |
| *G01N 11/10* | (2006.01) | |
| *G01N 9/00* | (2006.01) | |

(52) U.S. Cl.
CPC ............ *G01F 23/2967* (2013.01); *G01N 9/002* (2013.01); *G01N 9/32* (2013.01); *G01N 11/167* (2013.01)

USPC .......................... 73/290 V; 73/54.41; 73/32 A

(58) Field of Classification Search
CPC . G01N 9/002; G01N 11/16; G01N 2009/006; G01F 23/2967; G01F 23/2966
USPC ............... 73/290 V, 291, 54.01, 54.02, 54.23, 73/54.24, 54.41, 32 A, 32 R, 433
See application file for complete search history.

(56) References Cited

U.S. PATENT DOCUMENTS 4,240,285 A * 12/1980 Langdon ........................ 73/32 A
4,594,891 A    6/1986 Benz
(Continued)

FOREIGN PATENT DOCUMENTS

DE    3149464 A1    6/1983
DE    3215040 A1    11/1983
(Continued)

OTHER PUBLICATIONS

English translation of the IPR, WIPO, Geneva, Switzerland Jul. 21, 2010.

*Primary Examiner* — Daniel S Larkin
*Assistant Examiner* — Jamar Ray
(74) *Attorney, Agent, or Firm* — Bacon & Thomas, PLLC

(57) ABSTRACT

A multivariable sensor for determining and/or monitoring a predetermined fill level and density and/or viscosity of a liquid in a container. The sensor comprises a measuring tube provided in the container. The measuring tube has at least a first oscillatable segment and a second oscillatable segment, wherein the oscillatable segments have a cross sectional area deviating from a circularly round shape and at least one straight side, wherein on an inner wall of the oscillatable segments, driver/receiving units are placed, which cause the oscillatable segments to execute resonant oscillations. At least one control/evaluation unit is provided, which evaluates frequency and/or phase and/or amplitude of the oscillations and determines therefrom reaching of the predetermined fill level and density and/or viscosity of the liquid.

14 Claims, 3 Drawing Sheets

(56) References Cited

U.S. PATENT DOCUMENTS

| | | | |
|---|---|---|---|
| 4,922,745 A * | 5/1990 | Rudkin et al. | 73/32 A |
| 7,444,245 B2 * | 10/2008 | Pfeiffer et al. | 702/54 |
| 2007/0021931 A1 | 1/2007 | Pfeiffer | |
| 2010/0005865 A1 * | 1/2010 | Miura | 73/54.41 |

FOREIGN PATENT DOCUMENTS

| | | |
|---|---|---|
| DE | 3416254 A1 | 11/1985 |
| DE | 10138360 A1 | 2/2003 |

* cited by examiner

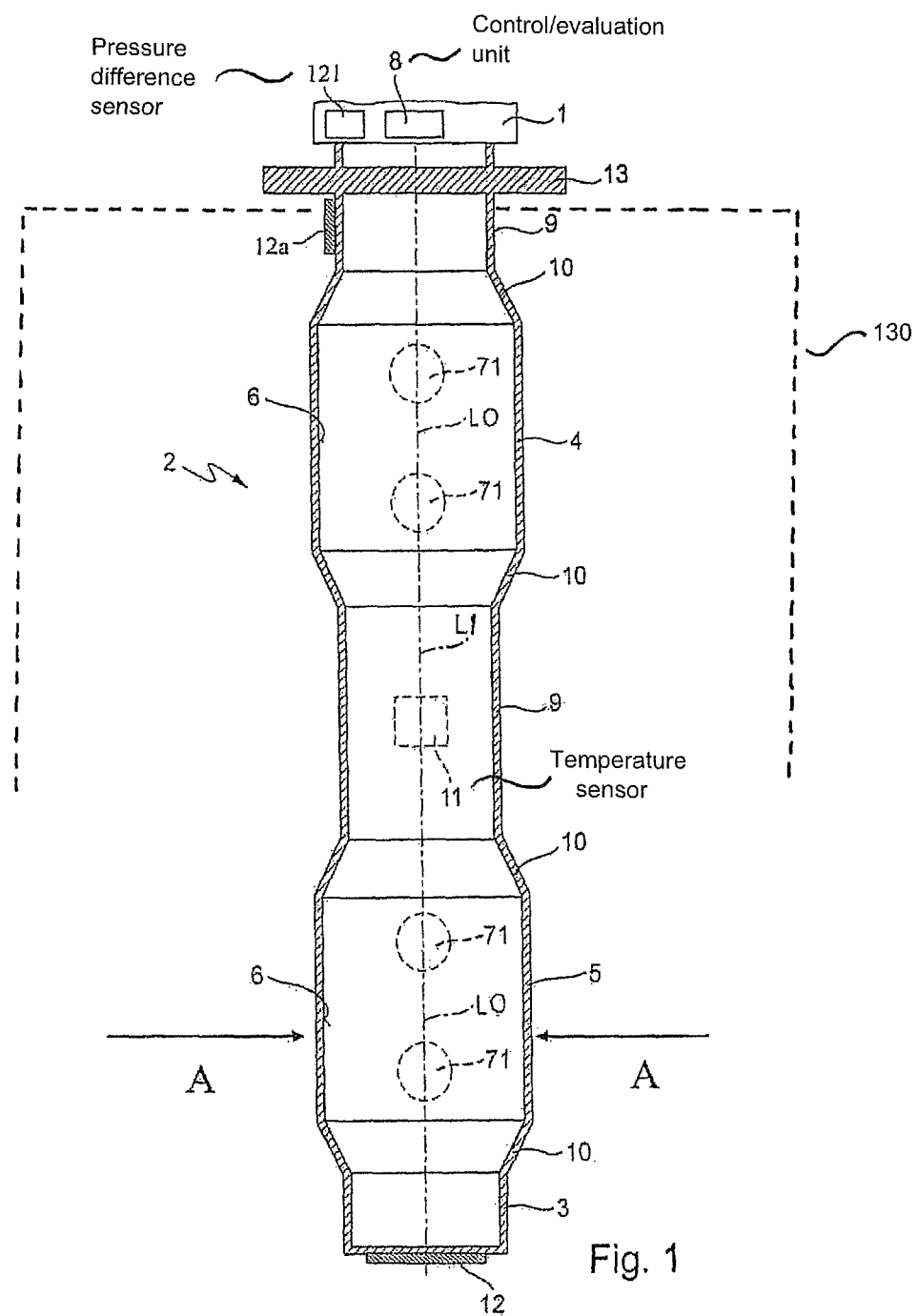

MULTIVARIABLE SENSOR FOR DETERMINING AND/OR MONITORING FILL LEVEL AND DENSITY AND/OR VISCOSITY OF A LIQUID IN A CONTAINER

TECHNICAL FIELD

The present invention relates to an apparatus for determining and/or monitoring a predetermined fill level and the density and/or the viscosity of a liquid in a container.

BACKGROUND DISCUSSION

For fill level measurement of a liquid or a bulk good in a container, so-called oscillatory forks are frequently used. In such case, there exist a number of different forms of embodiment, which differ mainly in the shape and length of the oscillatory fork. Such oscillatory forks are composed of two rods and are placed on a membrane, which is excited to oscillations by a drive unit. The two rods are thereby excited to opposite phase oscillations. The excitation is done with the resonance frequency of the oscillatory system. The oscillation is weakened when the oscillatory fork comes in contact with the measured medium. Due to the extra mass, which must be moved when the oscillating fork reaches into a liquid medium, the oscillation frequency decreases. In the case of media with lower density, such as, for example, gases, this effect is negligible. In the case of all viscous liquid media, a damping of the oscillation amplitude occurs as a result of friction. The amplitude change and/or frequency change is evaluated as a function of the medium. Additionally, the phase shift between the drive voltage and received voltage from the oscillatory rods moved to oscillations by the driving is evaluated, since this is likewise changed in the medium.

In containers, two such oscillatory forks are often applied, with one being placed in the lower region of the container and one in the upper region. In the normal state, the oscillatory fork mounted above oscillates in air, and provides an overflow protection, while the oscillatory fork mounted below oscillates in normal operation in the medium, and provides protection against running dry. Such oscillatory forks function excellently in liquids which do not form accretions and in bulk goods with small particle sizes relative to the oscillatory fork. In the case of media which form accretions on the oscillatory fork, after a certain accretion thickness, bridges form, which reach from the one rod to the other. These influence the oscillatory system and ultimately lead to the oscillatory rods no longer oscillating, and thus to measuring being no longer possible.

Oscillatory forks can also be applied for determining the density and/or the viscosity of a liquid medium. In order to be able unequivocally to determine a measured variable, it is, however, necessary to hold the boundary conditions constant and, respectively, to determine disturbance variables. An example of such boundary conditions or disturbing variables in the case of determining density and viscosity is fill level. In the determining of viscosity, a variable density of the medium, for example for reasons of temperature fluctuations, represents a disturbing variable. In order nevertheless to be able to determine viscosity, density is held constant, density is determined with a separate measuring device, or a measuring method is selected, which compensates for density dependencies. The latter is often connected with a large electronic effort. Often, it is not possible to hold the boundary conditions constant, so that at least a second measuring device is necessary for determining the disturbance variables. This requires at least one additional process connection, which not only brings with it extra costs, but also introduces hygienic risks, depending on the field of application.

In the case of bulk goods composed of coarse particles or liquids containing coarse particle, in the case of which the diameter of the particles is about equal to the distance between the two rods of the oscillatory fork, it occurs that particles jam between the rods. This, too, leads to a malfunctioning of the oscillatory fork. As a rule, in both cases, an error report is produced, which, for safety reasons, turns off the process.

A non-vibronic principle for fill level measurement of liquids is that wherein a rod is introduced into the container. The rod protrudes far into the container, and which is provided with a plurality of so-called floats. The floats then arrange themselves at a determined height corresponding to fill level of the liquid.

Due to the application of a plurality of floats on the rod, with this apparatus, not only a fill level can be determined, but also, for example, phase boundaries in the case of multiphase mixtures. A disadvantage in the case of this method is, however that the floats are susceptible to wear.

From the publication DE 3215040 C2, an apparatus for vibronic fill level measurement is known, which is composed of a measuring tube, which is introduced into the container and excited to oscillations by a drive lying in the interior of the measuring tube. The measuring tube is cylindrical, wherein the base is round or elliptical. A jamming of particles does not present a problem in the case of this apparatus. A disadvantage, however, is that, for exciting the measuring tube, relatively high frequencies are necessary, which strain the drive and the electronic components. Additionally, only low oscillation amplitudes are attainable.

SUMMARY OF THE INVENTION

An object of the invention is to provide an alternative apparatus for vibronic fill level measurement, in the case of which a jamming of the oscillatable unit or bridge building by particles contained in the measured medium is excluded, and which supplementally enables the determining of at least one additional process variable.

The object is achieved by features including that the apparatus has a measuring tube, which is introduced into the container, the measuring tube has at least a first oscillatable segment and a second oscillatable segment, the oscillatable segments have a cross sectional area deviating from a circularly round shape, on the inner wall of the oscillatable segments, driver/receiving units are placed, which cause the oscillatable segments to execute resonant oscillations, and at least one control/evaluation unit is provided, which evaluates frequency and/or phase and/or amplitude of the oscillations, and determines therefrom reaching of a predetermined fill level and density and/or viscosity of the liquid.

An advantage of the multivariable sensor is that both running dry protection as well as also overflow protection can be covered with only one device, by an oscillatable segment being formed, respectively, on the end of the measuring tube near the container floor and on the end of the measuring tube near the lid. It is also possible to provide an additional oscillatable segment in the middle of the measuring tube in such a manner, that, with its help, an additional fill level can be determined or a plausibility query can take place. If, for example, the running dry protection alarm signals and the middle segment still displays medium, an error is then present. Furthermore, fill level can be monitored with one of the segments, while a further segment serves for determining density of the medium. In the case of measured or known density, viscosity of the medium is moreover determinable with one oscillatable segment. Thus, the apparatus of the invention involves a multivariable sensor, which enables the determining of a large number of process variables with only one measuring device. This is especially advantageous, since only one process connection is required.

Due to the shape of the oscillatable segments deviating from a cylindrical shape and having at least one flat lateral surface, these oscillatable segments can be excited to oscillations with smaller frequencies, whereby large oscillation amplitudes can be achieved.

A further advantage of the multivariable sensor of the invention is the opportunity for application of additional sensors. If, for determining various process variables, independent devices are in each case introduced into the container, a corresponding number of connections are necessary. In contrast to this, in the case of integration of sensors for determining the desired process variables in the measuring tube, just one connector opening in the container suffices. For example, besides the oscillatable segments for vibronic fill level measurement, also a temperature sensor and at least one pressure sensor can be placed on the measuring tube. In such case, the position of the sensors is dependent on the respective application. If, for example, the temperature of the medium should be determined, in order to obtain a reliable measured value, the temperature sensor must be located at a position, which is covered by the medium. If a running dry protection is of concern to the measuring device, it is to be assumed that the end region of the measuring tube is continually covered with medium, so that the temperature sensor, in this case, is best placed in this end region. To assure that the pressure sensor determines the process pressure, it is preferably placed in the upper region, near the connection of the measuring tube to the container. It is likewise thinkable that a pressure sensor is placed, respectively, in the lower and in the upper regions of the measuring tube, or that the pressure sensitive elements of a pressure difference sensor are arranged in the lower and upper regions of the measuring tube, and the pressure difference is determined. This pressure difference is proportional to the hydrostatic pressure of the liquid in the container, so that fill level of the liquid is continually determinable therefrom.

In a first embodiment of the solution of the invention, the oscillatable segments have a cross sectional area, which is oval, elliptical or polygonal with an even number of sides, of which, in each case, two sides are parallel to one another, or the oscillatable segments have an essentially oval or elliptical basic form with two parallel sides. The symmetric shape is necessary for the purpose of decoupling the oscillatory system. However, measuring tubes are also thinkable, in the case of which a decoupling is not absolutely necessary, since only small coupling effects occur. This is the situation in the case of oscillatable segments, which have a low mass in comparison to neighboring intermediate segments. In an alternative embodiment, the cross sectional area is, consequently, preferably oval or elliptical, with a straight side. The oscillatable segments then have only one flat, lateral surface, which is excited to oscillations by a driver/receiving unit. The cross sectional area can then also be a polygon with an uneven number of sides.

Due to the at least one flat, lateral surface, the stiffness of the oscillatable segment is reduced, and furthermore, the installation of the driver/receiving unit is facilitated. The lessened stiffness of the oscillatable segment as compared to a cylindrical tube segment has the result that the frequency necessary for resonant exciting of the oscillatable segment is lower, so that the electronic components and the driver/receiving unit are exposed to smaller loadings, or a low power consumption occurs. Furthermore, due to the low frequencies, maximum oscillation amplitudes are reached. All oscillatable segments preferably have the same shape. Segments lying between the oscillatable segments are preferably embodied with circular cross sections. The oscillatable segments then have connector regions, in which the different cross sections are adapted to one another.

In a further development of the multivariable sensor of the invention, the measuring tube has at least three segments, wherein at least two segments are embodied as oscillatable segments, wherein at least one segment is embodied as an intermediate segment with a circularly round cross sectional area and wherein the oscillatable segments have transition regions, which serve for adapting the shape of the cross sectional area of the at least two oscillatable segments to the circularly round cross sectional area of the at least one intermediate segment.

In a further development of the solution of the invention, the longitudinal axes of the oscillatable segments and the longitudinal axes of the intermediate segments lie on a shared line. In alternative embodiments, the oscillatable segments are at least partially eccentrically arranged. This can be required, for example, when an impediment, which must be bypassed, is located in the container.

In a further development of the method of the invention, the driver/receiving unit is a piezoelectric drive. This is placed symmetrically on the inner wall of the oscillatable segment. The piezoelectric drive is preferably embodied as a stack drive.

In the case of an additional further development of the invention, the driver/receiving unit is embodied as an electrodynamic drive. The drive elements of the electrodynamic drive are electromagnetic, electrostatic or magnetostrictive drive elements. The electrodynamic drive is placed on the inner wall of the oscillatable segment. In a further development of the solution of the invention, a number of drive elements are arranged pairwise on the inner wall of the oscillatable segments on oppositely lying sides of the oscillatable segment and symmetrically with respect to the longitudinal axis of the oscillatable segment.

In an additional further development of the invention, the drive elements of the driver/receiving units are placed on the inner wall of the oscillatable segments in such a manner that two oppositely lying sides of the oscillatable segments execute opposite phase oscillations.

A further development of the multivariable sensor of the invention includes the feature that a temperature sensor is placed on the measuring tube in such a manner that it does not impede the oscillations of the oscillatable segments. For example, knowledge of the reigning temperature is necessary for detecting accretion formation or for density measurement. By mounting the temperature sensor on the measuring tube, no separate measuring device is necessary. This saves an additional flange or connection. Additionally, the measurement data of the temperature sensor can be processed with the data of the oscillatable segments in a shared control/evaluation unit.

A further development of the invention provides that the measuring tube has at least one pressure sensor. For pressure measurement, a pressure sensor is preferably placed on the lower end of the measuring tube protruding into the container. Preferably, two pressure sensors or the pressure sensitive elements of a pressure difference sensor are arranged in respective end regions of the measuring tube, so that pressure difference is determinable. Due to the relationship between pressure difference and hydrostatic pressure, this enables continuous fill level measurement.

A further development of the solution of the invention lies in features that the measuring tube has two oscillatable segments, which are spaced apart from one another by an intermediate segment, and which in each case have a driver/receiving unit, which causes them to execute oscillations, and that the measuring tube is matched in length and in position of the oscillatable segments to the container in such a manner that the first oscillatable segment detects a maximal fill level and the second oscillatable segment detects a minimum fill level.

In an example of an embodiment, it is provided that the measuring tube has at least two oscillatable segments, which are spaced apart from one another by an intermediate segment, and which in each case have a driver/receiving unit, which causes them to execute oscillations, and the measuring tube is matched in length and in position of the oscillatable segments to the container in such a manner, that, based on the oscillations of the oscillatable segments, the control/evaluation unit determined density and/or viscosity of the medium at different predetermined heights.

Another further development of the invention lies in the fact that the control/evaluation unit successively activates and reads out the driver/receiving units of the oscillatable segments and, in given cases, additionally placed sensors, and determines the respective process variables.

If, for example, two oscillatable segments are provided for determining a minimum and a maximal fill level and for determining density of the measured medium, as well as an intermediate segment with a temperature sensor, and if a pressure measuring cell is arranged in the end region of the measuring tube, the control/evaluation unit then successively determines the variables "maximum fill level reached?", "density 1", "current temperature", "minimum fill level reached?", "density 2" and "current pressure" in a sequence matched to the process or in a predetermined sequence.

BRIEF DESCRIPTION OF THE DRAWINGS

The invention will now be explained in greater detail on the basis of the appended drawing, the figures of which show as follows:

FIG. 1 a multivariable sensor of the invention with two oscillatable segments;

FIG. 2b a detail view of an oscillatable segment, wherein the view is rotated by 90° with respect to the longitudinal axis in comparison to the view of FIG. 2a.

DETAILED DISCUSSION IN CONJUNCTION WITH THE DRAWINGS

Figure 1A:
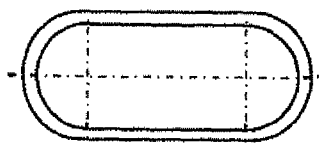
FIG. 1a schematically, a cross section of an oscillatable segment according to FIG. 1.

FIG. 1 shows a multivariable sensor with a first oscillatable segment 4, a second oscillatable segment 5 and an intermediate segment 9. On the intermediate segment 9, a temperature sensor 11 is arranged, and in the end region 3 of the measuring tube 2, a pressure sensor 12 is arranged. The oscillatable segments 4, 5 and the intermediate segment 9 are, in such case, arranged in such a manner that the longitudinal axes LO of the oscillatable segments 4, 5 and the longitudinal axis LI of the intermediate segment 9 lie on a shared line.

The length of the intermediate segment 9 is matched to the dimensions of the container 130 in such a manner that the second oscillatable segment 5 lies at the height, which corresponds to the minimum fill level. The segment between flange 13 and first oscillatable segment 4 is chosen as regards its length in such a manner that the first oscillatable segment 4 serves for monitoring the maximal fill level. Alternatively, the lengths of the particular segments are selected in such a manner that either a maximum or a minimal fill level is monitorable, and furthermore, density and/or viscosity of the medium at a determined height are/is determinable. In alternative embodiments, other oscillatable segments are thinkable, which are arranged in the container 130 at heights between the minimum and the maximal fill level height, so that also fill levels lying therebetween are determinable, or density and/or viscosity of the medium at these positions are/is uniquely determinable. Advantageously, a second pressure sensor 12a is arranged in the upper region of the measuring tube 2 near the process connection, so that this sensor is not covered with medium. By determining the difference between the pressure reigning at the site of the second pressure sensor 12a and the pressure reigning at the site of the pressure sensor 12 arranged on the lower end region of the measuring tube 2, in addition to the simple pressure determination with the pressure sensor 12, a continuous fill level measurement is possible. Alternatively, a pressure difference sensor 121 is arranged near the process connection, neighboring or in the housing 1 of the multivariable sensor. The pressure sensor 12 and the second pressure sensor 12a are then two pressure sensitive elements, e.g. in the form of membranes. Connected with the pressure sensitive elements are supply lines (not shown), which supply the pressure acting on the particular pressure sensitive element to the pressure difference sensor 121. The supply lines are arranged in the interior of the measuring tube 2.

Figure 1B:
FIG. 1b schematically, an alternative cross sectional shape of an oscillatable segment.

In this preferred example of an embodiment, the cross sectional areas of the oscillatable segments 4, 5 are oval, with two parallel sides. A representation of the cross section of the oscillatable segment 5 in the cutting plane A-A shown in FIG. 1 is given in FIG. 1a. The outline of the cross section is thus like the course of a stadium track. In alternative forms of embodiment, the cross sectional area is oval, with only one straight side; elliptical, having at least one straight side, or polygonal, with an even number of sides, wherein these sides are preferably pairwise parallel to one another. An example of a cross section with only one straight side is presented in FIG. 1b. In the embodiment illustrated in FIG. 1 and FIG. 1a, the oscillatable segments 4, 5 have, in each case, two parallel side surfaces. Preferably, in this region, on the inner side 6 of the oscillatable segments 4, 5, the drive elements 71 of the driver/receiving unit 7 are arranged. Due to the planarity of the side surfaces, the stiffness of the side surfaces is reduced, so that smaller frequencies are necessary for oscillation excitement as compared to curved surfaces. This is advantageous for the electronic components of the apparatus of the invention, since the power consumption is smaller, and additionally, large oscillation amplitudes can be achieved. The intermediate segment 9 preferably has a circularly round cross sectional area. For adapting the cross sectional area of the oscillatable segments 4, 5 to those of the intermediate segment 9, transition regions 10 are provided, in which the cross sectional areas are gradually matched to one another.

In this example of an embodiment, the end region 3 of the measuring tube 2 is embodied as an intermediate segment 9 with a circularly round cross sectional area. In alternative embodiments, the end region 3 takes other forms or does not form a separate segment, but is instead formed by the second oscillatable segment 5. The end region is preferably closed.

For connecting the multivariable sensor to the container 130, a flange 13 is placed on measuring tube 2. Of course, the sensor can also have a connection for an alternative type of connecting, such as, for example, a screw thread. Presented in this Fig. only schematically is a housing 1, which is arranged above the connection, outside of the container 130, and includes electronic components such as the control/evaluation unit 8.

Figure 2A:
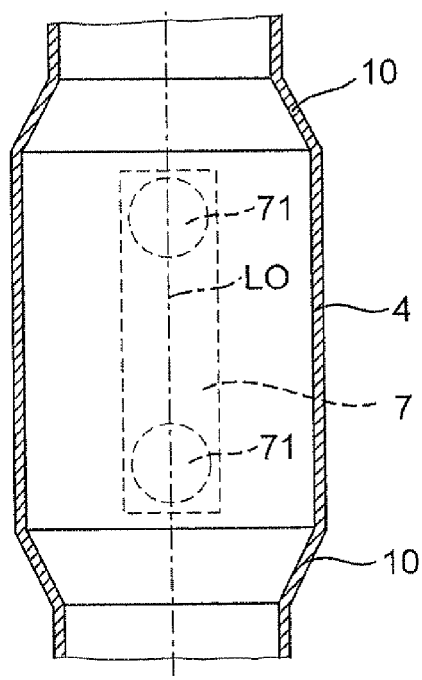
FIG. 2a a detail view of an oscillatable segment.
Figure 2B:
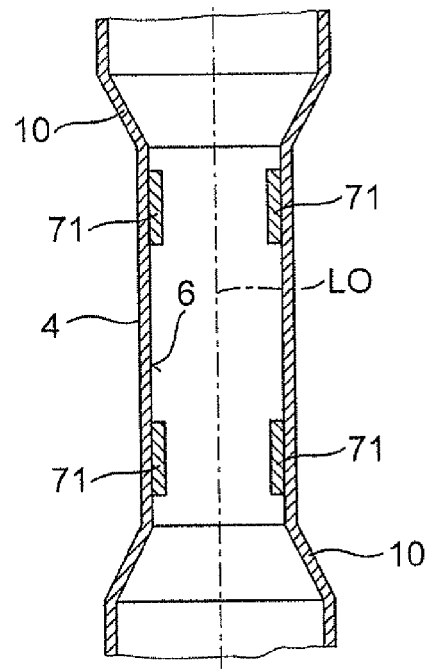

FIGS. 2a and 2b show a detail view of an oscillatable segment 4, 5 of FIG. 1. FIG. 2a shows a front view, i.e. onto one of the flat side surfaces of the oscillatable segment 4, 5, and FIG. 2b shows a side view rotated by 90° with respect to FIG. 2a. The drive elements 71 of the driver/receiving unit 7 are, in such case, placed on the inner side 6 of the oscillatable segment 4, 5. This example of an embodiment involves four drive elements 71, wherein, in each case, two are arranged lying opposite each other on the flat side surfaces. This number is only a preferred form of embodiment; another number of drive elements 71 is also possible. Important is that the arrangement of the drive elements 71 on the inner side 6 of the oscillatable segment 4 always occurs symmetrically, so that the number of the drive elements 71 is even.

The drive elements 71 are preferably piezoelectric elements, wherein, in an embodiment, the drive elements also serve for receipt of the oscillation signals. In an alternative embodiment, drive elements are provided, which only serve for the driving of the oscillatable segment 4, and receiver elements are provided, which only serve for the receipt of the oscillation signals of the oscillatable segment 4. The piezoelectric driver/receiving unit can equally be embodied as a bimorph drive or as a stack drive. However, magnetostrictive, electrostatic or electromagnetic drive elements 71 are also thinkable. The arrangement of the drive elements 71 is, in such case, selected in such a manner that the sides, on which they are applied, execute opposite phase oscillations with the resonance frequency of the oscillatable segment 4, 5. In the case of the covering or at least partial covering of the oscillatable segment 4, 5 with liquid medium, the oscillation frequency is reduced for reasons of the increased moved mass. This change is, for example, detected by the same piezoelectric elements, which also form the drive elements 71.

On the basis of this received signal, the control/evaluation unit 8 produces a switching signal, which indicates the free or covered state of the respective oscillatable segment 4, 5. In an embodiment, based on the oscillations of the oscillatable segment 4, as well as the information concerning fill level gained with the oscillatable segment 5, the control/evaluation unit 8 ascertains other process variables such as density and/or viscosity. Viscosity is preferably determined according to one of the methods described in WO 2009037050 A1 or DE 10050299 A1. On the basis of these considerations, viscosity determination occurs, for example, by excitation to resonant oscillations being briefly interrupted and the decay constant being evaluated, or by means of a frequency-phase diagram. Density is, as a rule, determined by evaluating the oscillation frequency. The higher density of the medium, the lower is the resonance frequency, so that a change in density of the medium can be ascertained from a change in the resonance frequency. For this, however, it is necessary to assure that a change in the oscillation frequency is to be attributed to a change density and not to a change in fill level. With the apparatus of the invention, this is directly possible, since density is determinable with the oscillatable segment 5 arranged at a lower height in the container 130, while, with the oscillatable segment 4 arranged further above in the container 130, fill level can be monitored. So long as the oscillatable segment 4 is covered by medium, density or viscosity can be determined with the oscillatable segment 5 arranged below. In an embodiment, a third oscillatable segment is provided, so that density and viscosity are determinable in each case with a separate oscillatable segment. Alternatively, the control/evaluation unit 8 is embodied in such a manner that the oscillatable segments 4, 5 are differently excitable, or their oscillations are correspondingly evaluable, as a function of the process variable to be determined.

The invention claimed is:

1. A multivariable sensor for determining or monitoring at least one predetermined fill level and density or viscosity of a liquid in a container, comprising:
    a measuring tube provided in the container, said measuring tube has at least a first oscillatable segment and a second oscillatable segment, said oscillatable segments have a cross sectional area deviating from a circularly round shape and at least one straight side, wherein, on an inner wall of said oscillatable segments, driver/receiving units are placed, which cause the oscillatable segments to execute resonant oscillations; and
    at least one control/evaluation unit, which evaluates frequency or phase or amplitude of the oscillations, and determines therefrom reaching of a predetermined fill level and density or viscosity of the liquid; wherein
    said measuring tube has two oscillatable segments, which are spaced apart from one another by an intermediate segment, and which have a driver/receiving unit respectively, which causes said oscillatable segments to execute oscillations; and
    said measuring tube is matched in length and in position of said oscillatable segments to the container in such a manner that the first oscillatable segment detects a maximal fill level and the second oscillatable segment detects a minimum fill level.

2. The multivariable sensor as claimed in claim 1, wherein:
    said oscillatable segments have a cross sectional area, which is oval, elliptical or polygonal with an even number of sides where two sides are parallel to one another, or wherein said oscillatable segments have an essentially oval or elliptical basic form with two parallel sides.

3. The multivariable sensor as claimed in claim 1, wherein:
    said measuring tube has at least three segments, at least two segments are embodied as oscillatable segments, and at least one segment is embodied as an intermediate segment with a circularly round cross sectional area; and said oscillatable segments have transition regions, which serve for adapting the shape of the cross sectional area of said at least two oscillatable segments to the circularly round cross sectional area of said at least one intermediate segment.

4. The multivariable sensor as claimed in claim 3, wherein:
    the longitudinal axes of said oscillatable segments and the longitudinal axes of said intermediate segments lie on a shared line.

5. The multivariable sensor as claimed in claim 1, wherein:
    said driver/receiving unit comprises piezoelectric drive elements.

6. The multivariable sensor as claimed in claim 5, wherein:
    on the inner wall of said oscillatable segments, a number of drive elements are arranged pairwise on oppositely lying sides of said oscillatable segment and symmetrically to the longitudinal axis of said oscillatable segment.

7. The multivariable sensor as claimed in claim 5, wherein:
    said drive elements of said driver/receiving units are placed on the inner wall of said oscillatable segments in such a manner that two oppositely lying sides of said oscillatable segments execute opposite phase oscillations.

8. The multivariable sensor as claimed in claim 1, wherein:
said driver/receiving unit comprises electromagnetic, electrostatic or magnetostrictive drive elements.

9. The multivariable sensor as claimed in claim 1, wherein:
said measuring tube is closed on the end region located in the container.

10. The multivariable sensor as claimed in claim 1, wherein:
a temperature sensor is placed on said measuring tube in such a manner that it does not impede oscillations of said oscillatable segments.

11. The multivariable sensor as claimed in claim 1, wherein:
said measuring tube has at least one pressure sensor or a relative pressure sensor.

12. The multivariable sensor as claimed in claim 1, wherein:
said measuring tube has at least two of said oscillatable segments, which are spaced apart from one another by an intermediate segment, and which have a driver/receiving unit respectively, which causes said oscillatable segments to execute oscillations; and
said measuring tube is matched in length and in position of said oscillatable segments to the container in such a manner that, based on the oscillations of said oscillatable segments, said control/evaluation unit determines density or viscosity of the medium at different predetermined heights.

13. The multivariable sensor as claimed in claim 1, wherein:
said control/evaluation unit successively activates and reads out said driver/receiving units of said oscillatable segments and determines the respective process variables.

14. The multivariable sensor as claimed in claim 13, wherein:
said control/evaluation unit successively activates and reads out additionally placed sensors, and determines the respective process variables.

* * * * *